United States Patent [19]

Barberet et al.

[11] Patent Number: Plant 5,530

[45] Date of Patent: Aug. 6, 1985

[54] CARNATION NAMED LONDAXIE

[75] Inventors: Nicole Barberet; Yves Ducloux, both of Antibes, France

[73] Assignee: Laboratoire de Physiologie Vegetale de la Londe, Antibes, France

[21] Appl. No.: 512,884

[22] Filed: Jul. 11, 1983

[51] Int. Cl.[3] ..... A01H 5/00

[52] U.S. Cl. ..... Plt./71

[58] Field of Search ..... Plt./71

*Primary Examiner*—Robert E. Bagwill

*Attorney, Agent, or Firm*—Chas. W. Rummler

[57] ABSTRACT

A new and distinct variety of carnation of the tall, monoflore type characterized by the unique color of its medium sized blooms which are borne on long, stiff stems, the color being intermediate that of the similar flower of "Barlo II", U.S. Plant Pat. No. 3,406, and "Baruklo" (unpatented), furthermore this new variety has a more serrated petal and a stiffer stem than those of the named varieties; the new plant is also distinguished by its vigorous, upright and tall growth habit with moderately abundant foliage and profusely produced blossoms during each of its recurrent blooming seasons.

1 Drawing Figure

BACKGROUND OF THE NEW PLANT

Our new carnation cultivar is the result of breeding efforts carried on by us since 1978 with the object of developing new and distinctive varieties of carnations having attractive color and good quality of flower form and plant growth habits. This new plant originated as a seedling produced at La Londe, France, by a cross of selected and individually identified plants growing among breeding stock maintained by us at La Londe, and this plant was selected by us for propagation and test because of its unique coloration and apparently advantageous growth habit. The discovery plant was propagated by us at La Londe, France, by means of cuttings, and the newly propagated plants appeared to possess all of the distinctive characteristics of the parent plant. Continued propagation under our direction, by means of cuttings, through several successive generations, has demonstrated that the novel and distinctive characteristics of this new plant hold true from generation to generation and appear to be firmly fixed.

DESCRIPTION OF THE DRAWING

Our new carnation cultivar is illustrated by the accompanying photographic drawing which shows, in full color, a typical arrangement of buds, partially opened flowers and full blooms, the color rendition being as nearly true, as herein specified, as it is reasonably possible to obtain by conventional photographic procedures.

DESCRIPTION OF THE NEW PLANT

The following is a detailed description of our new carnation variety based upon characteristics of greenhouse grown plants observed at La Londe, France, in the Spring of 1983, the color designations being according to The R.H.S. Colour Chart of The Royal Horticultural Society at London, England.

THE PLANT

Origin: Seedling.

Parentage:

*Seed parent.*—Stock Variety No. 72 L 3 (unpatended).

*Pollen parent.*—Stock Variety No. 83-91 P (unpatented). These unnamed varieties are individually identified in our permanent records and are included in our collection of carnation plants maintained for breeding purposes at La Londe, France.

Classification:

*Botanic.*—*Dianthus caryophyllus.*

*Commercial.*—Standard Carnation.

Form: Tall and erect bush.

Height: Average of 112 cm. at eight months.

Main stem: Less than 15 cm. long due to pinching.

Branching character: This plant has at least four stems emitted near the ground.

Growth habit: Vigorous, strong and upright with rather rigid stems.

Foliage:

*Quantity.*—Moderately abundant with more than 120 leaves.

*Leaf size.*—Averaging about 12.9 cm. in length and about 9 mm. in width, measured at the seventh node.

*Leaf shape.*—Linear with rolled margins and acuminate tip.

*Texture.*—Leathery.

*Color.*—Upper side — 189A. Under side — 189A.

*Ribs, veins and rachis.*—Hardly noticeable.

THE BUD

Size: Medium. Diameter averages about 1.9 cm. Length averages about 3.3 cm.

Form: Urn shaped and short.

Opening rate: Normal for carnations.

Color of petals:

*When sepals first divide.*—50D.

*When petals begin to unfurl.*—50D and 49A.

Sepals:

*Number.*—Five (exceptionally six).

*Shape.*—Joined at the lower part and with ovate character at the upper part which has a sharply pointed apex. Sepals are hooded over the bud and stand up when the flowers open.

*Color.*—Inside — Greenish White. Outside — 189C.

Calyx:

*Shape.*—Bell shaped and relatively short.
*Size.*—Large.
*Splitting.*—The calyx does not split.
*Aspect.*—Smooth.

Flower stem:
*Length.*—About 77 cm.
*Character.*—Erect and rather rigid.
*Color.*—189A and 189B.

THE FLOWER

Blooming habit: Recurrent and profusely in midseason of Spring and Fall.

Size of bloom: Medium.
*Diameter.*—Averages about 8.9 cm.
*Depth.*—Averages about 6.5 cm.

Borne: Singly.

Shape:
*When bloom first opens.*—High centered.
*When bloom matures.*—Ball shaped.

Petalage:
*Number.*—From 66 to 81, averaging about 67.
*Arrangement.*—Imbricated.
*Form.*—Fan shaped with rounded edges.
*Texture.*—Soft.
*Appearance.*—Satiny.
*Color.*—Outer petal: Upper side — Body — 49A. Base — Greenish. Reverse side — 50D. Inside Petal: Upper side — Body — 49A. Base — Greenish. Reverse side — 50D.

Petaloids:
*Number.*—From 1 to about 11.
*Size.*—Smaller than petals.
*Color.*—The same as the petals.

Flower stem:
*Length.*—About 77 cm. (cut at tenth node).
*Character.*—Upright and with good strength.
*Color.*—189A and 189B.

Fragrance: Perceptible.

Persistence: The petals hang on and dry.

Lasting quality:
*As a cut flower.*—At least 10 days in vase keeping.

Disease resistance: Plant appears to be resistant to *Fusarium oxysporum* as observed INRA, Antibes, Alpes-Maritimes, France.

REPRODUCTIVE ORGANS

Stamens:
*Number.*—8 to 19 arranged around the pistils.
*Anthers.*—Size: Less than 4 mm. Color: Whitish.
*Filaments.*—Color — Whitish.

Pistils:
*Number.*—4 to 6.
*Styles.*—Color — White.
*Stigmas.*—Color — White.

Character of ovaries: The ovary is ribbed.

Our new carnation hybrid is unique in its flower coloration and compared with the most similar varieties, our new plant is of intermediate color with a more serrated petal and a stiffer stem.

We claim:

1. A new and distinctive carnation cultivar, substantially as herein shown and described, characterized by the unique coloration of its medium sized blooms and its abundant production of flowers during each of its recurrent blooming seasons.

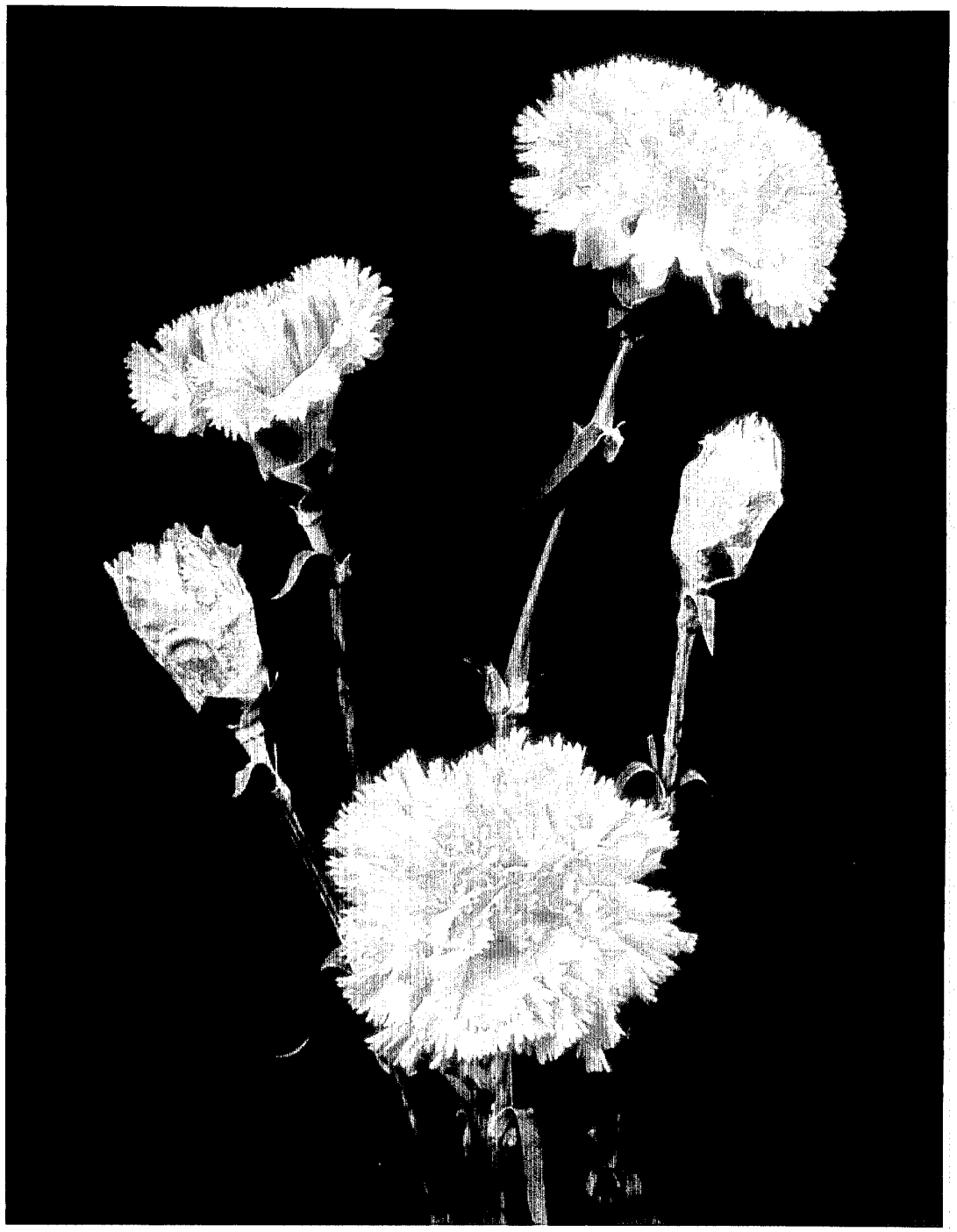

* * * * *